United States Patent [19]

Rinaudo et al.

[11] 4,431,734
[45] Feb. 14, 1984

[54] ENZYMATIC PROCESS FOR THE TREATMENT OF XANTHAN GUMS TO IMPROVE THE FILTRABILITY OF THEIR AQUEOUS SOLUTIONS

[75] Inventors: Marguerite Rinaudo, Grenoble; Michel Milas, Eybens; Norbert Kohler, Le Chesnay, all of France

[73] Assignee: Institut Francais du Petrole, Rueil-Malmaison, France

[21] Appl. No.: 381,610

[22] Filed: May 24, 1982

[30] Foreign Application Priority Data

May 22, 1981 [FR] France ................................ 81 10403

[51] Int. Cl.$^3$ ...................... C12P 19/06; C12P 39/00; C13L 3/00; E21B 43/22
[52] U.S. Cl. ..................................... 435/104; 435/42; 435/274; 166/246
[58] Field of Search ...................... 435/104, 101, 274; 166/246

[56] References Cited

U.S. PATENT DOCUMENTS 4,010,071  3/1977  Colegrove ...................... 435/274 X
4,326,037  4/1982  Griffith et al. ...................... 435/247

FOREIGN PATENT DOCUMENTS 39962  11/1981  European Pat. Off. ............ 435/104

*Primary Examiner*—Lionel M. Shapiro
*Attorney, Agent, or Firm*—Millen & White

[57] ABSTRACT

The filtrability of xanthan gum aqueous solutions is improved by an enzymatic treatment in two successive steps, the first step by means of a polysaccharase and the second step by means of a protease, the operating conditions of each step being such that the corresponding enzyme is active in said step.

19 Claims, 1 Drawing Figure

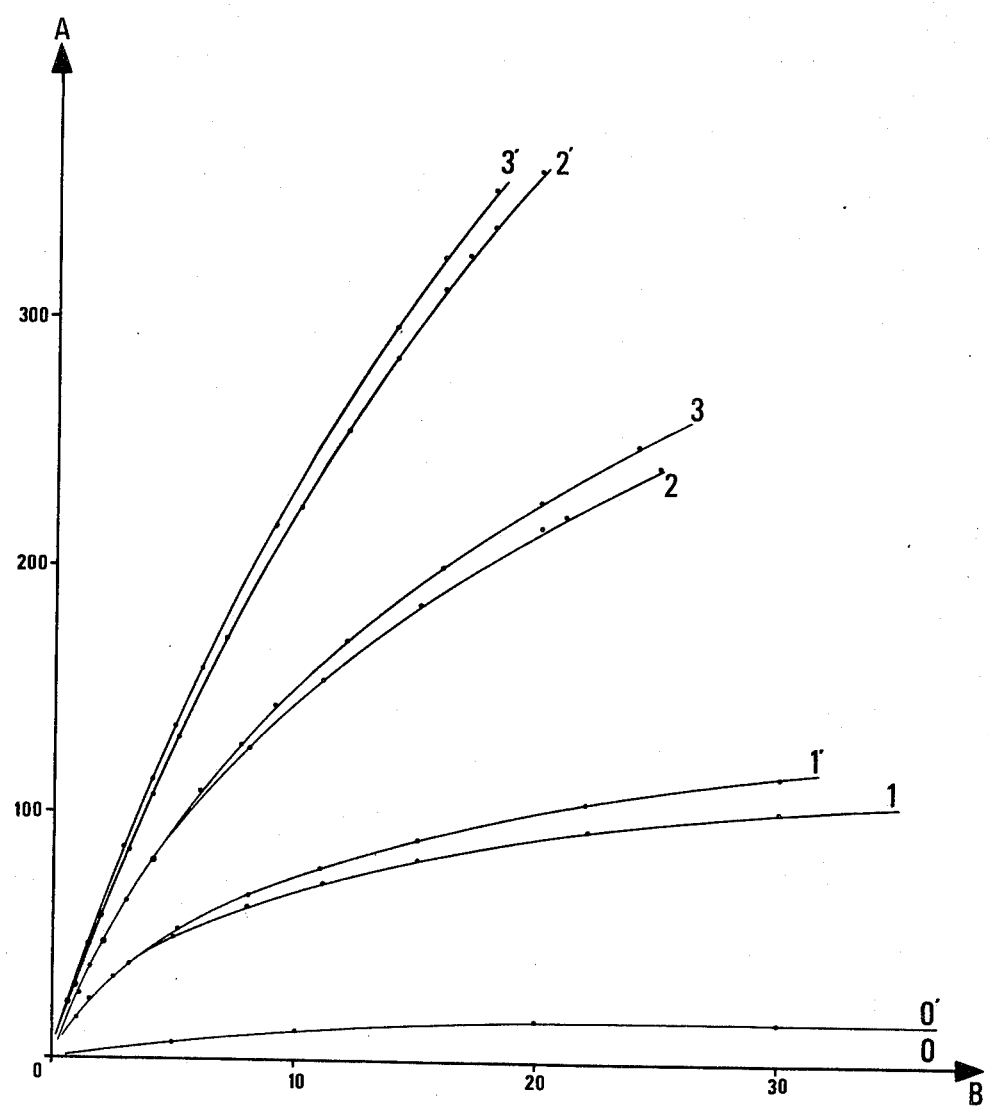

ENZYMATIC PROCESS FOR THE TREATMENT OF XANTHAN GUMS TO IMPROVE THE FILTRABILITY OF THEIR AQUEOUS SOLUTIONS

The present invention concerns an improvement to the injectivity and filtrability of aqueous xanthan gum solutions, during their injection and their circulation through petroleum formations, in view of improving the recovery rate of crude oil; more particularly, it concerns a suitable treatment with two successive enzymatic systems, one of the polysaccharase or glucanehydrolase type at an acid or substantially neutral pH, on the one hand, and the other of the protease type at a basic, neutral or acid, pH, on the other hand, to obtain limpid solutions of these xanthan gums whose injectivity and flow through the petroleum formations occurs without loss in the intrinsic properties of the polysaccharide and in particular in its thickening character.

STATE OF THE ART

Xanthan gums are hydrophilic polysaccharides obtained by fermentation of convenient nutrients based on carbohydrates under the action of specific micro-organisms, particularly bacteria pertaining to the Xanthomonas genus. The xanthan gum was found to be useful in many applications both in the food industry and in the petroleum field. An important application consists of the use of the xanthan gums for displacing the oil of partially depleted crude oil reservoirs.

The xanthan gums form a thickening agent particularly useful in this latter application. As a matter of fact, they are characterized by a high insensitivity to the salinity and to the nature of the salts, particularly they do not precipitate and do not lose their viscosity under normal conditions of use and, also, by a high stability to mechanical stresses. However, these xanthan gums also suffer from defects, the most important of which is that they quickly plug the petroleum formation at the immediate vicinity of the injection well and thus impede any flushing of said formation and, consequently, any additional oil extraction or recovery.

The reasons for this plugging or bad injectivity are numerous. On the one hand, the raw fermentation broths as well as the xanthan gums precipitated and separated from the fermentation broths, contain a certain number of insoluble particles resulting from the fermentation, such as bacteria cells or other cell fragments whose separation from the fermentation juice or from aqueous dispersions of xanthan gums is made difficult essentially as a result of the huge viscosities encountered. On the other hand, the aqueous solutions of xanthan gums, freed from their insoluble components by means of various known techniques such as the filtration at high pressure gradients through calibrated filters or through diatomaceous earths, have still a plugging effect at a relatively small distance from the injection well, where the pressure gradients become negligible and the flow velocities very low. As a matter of fact, the aqueous solutions of xanthan gums still contain, after the removal of the insoluble particles by a so-called clarification process, a certain number of translucent aggregates, deformable under the action of the high stresses prevailing at the inlet of the formations near the injection well and which, above all, are not removable by mere filtration or centrifugation of these aqueous solutions. The presence of said aggregates, also called microgels, seems to be favoured by inadequate conditions of separation and precipitation of the powdered polysaccharide from the fermentation juice.

The injectivity tests for estimating the capacity of the raw solution of xanthan gum to penetrate the first centimeters of the formation in the vicinity of the injection well are well known and the detailed conditions of these tests are described, for example, in the article of G. E. Tinker, R. W. Bowman and G. A. Pope "Determination of in-situ Mobility and Wellbore Impairment from Polymer Injectivity Data", Journal of Petroleum Technology, May 1976, pages 586 to 596.

A first way of conducting the test consists of measuring, versus time, the accumulated volume of filtrate of the polysaccharide solution passing through a calibrated filter of 47 mm diameter or still of 142 mm diameter and whose pore size ranges from 0.45 to 5.0 $\mu$m under a constant manometric pressure from 10 kPa to 300 kPa, thus simulating both the pore size of the formation around the injection well and the high pressure drops encountered therein.

Generally, in the following detailed examples, the injectivity test will be conducted through a 0.8 $\mu$m Millipore filter of a 47 mm diameter, under a constant manometric pressure of 10 kPa.

The detection of the microgels present in the aqueous solutions of xanthan gums may be effected by means of the so-called flowing or filtrability test as described in the article of N. Kohler and G. Chauveteau "Xanthan Polysaccharide Plugging Behaviour in Porous Media-Preferential Use of Fermentation Broth"—Journal of Petroleum Technology, February 1981, pages 349 to 358. This test is characterized by the injection at constant flow rate, by means of a double effect pump, of a purified xanthan gum solution through one or more calibrated filters of a pore diameter larger than 0.8 $\mu$m, for example through filters with pores of a 3 $\mu$m diameter. This injection is preferably effected at velocities corresponding to those encountered in the field inside the formation, typically smaller than one meter per day. By means of a differential pressure sensor, the pressure drops on each side of the filter are recorded versus time for the polymer solution as compared with the aqueous phase used for solubilizing the latter: $\Delta P$ polymer/$\Delta P$ water. This ratio of the pressure drops of the polymer solution to those of water during the circulation through the same porous medium (filters or natural porous media) is also called mobility reduction $R_\lambda$. Another characteristic magnitude which must be usefully controlled during such flowing of polymer solutions through aqueous media, is the relative viscosity $\eta_r$, ratio of the respective viscosities of the polymer solution and of the solubizing water, whose value must not vary or only vary to a small extent during such flowing experiments.

A correct estimation of the penetration and circulation capacity of a polysaccharide solution inside a petroleum formation must resort to the two above mentioned tests, i.e. an injectivity test for estimating the plugging at the inlet of the formation by the insoluble particles and also a flowing or filtrability test at constant but low flow rate for estimating the plugging, if any, due to the microgels, at a certain distance from the injection well.

The use of enzymes has been proposed in order to avoid the limitations of use of aqueous solutions of xanthan gums and to improve their injectivity and filtrability. The U.S. Pat. Nos. 4,010,071, 4,119,491, and 4,165,257 describe processes for the clarification of raw fermentation juices or aqueous solutions obtained by dispersion of powdered xanthan gums, by means of an enzyme of the protease type. The treatment takes place preferably in a strongly basic medium (7.5<pH<13) and at temperatures lower than 60° C.

A low salinity of the water and, in particular, a content of bivalent ions smaller than 100 ppm is recommended. In addition, it is advisable to filter, for example through diatomaceous earth, the so-treated xanthan gum solutions, in order to avoid losses of injectivity as a result of the plugging of the formations by imperfectly solvated protein materials. This treatment by means of an enzyme of the protease type, although resulting in noticeable improvements as compared to untreated solutions, does not permit to overcome, without further filtration, the plugging problems resulting from the presence of insoluble protein-free inorganic or organic materials and no mention is made of the possible action of these enzymes of the protease type on the microgels. Moreover, the use of strongly basic pH values (pH>9) is liable to produce the transformation of the primary structure of the xanthan gum and a depolymerization.

The U.S. Pat. No. 4,094,739 proposes to clarify the fermentation broths obtained from Xanthomonas Campestris, whose microbial cells have first been deactivated by pasteurization before solubilization, by a second fermentation with a microorganism of the fungus type, in the presence of additional glucose, of the residual Xanthomonas cells, initially difficultly filtrable, due to their small size, by producing insoluble cells of a much greater size which are more easily filtrable. This treatment consequently requires a preliminary filtration of said cells and no indication is given as concerns the improvement in injectivity and filtrability of the obtained solutions.

Applicants' corresponding French patent specification No. 80/21 395, corresponding to U.S. Ser. No. 309,147, has for object to improve both the injectivity and the filtrability of xanthan gum solutions in the petroleum formations, by means of an enzymatic system of the polysaccharase or glucane-hydrolase type. This enzymatic process, which is preferably carried out in a slightly acid pH medium and in water of high salinity, gives limpid solutions of said xanthan gums, whose injectivity and flowing through the petroleum formations are not subject to any loss of the intrinsic properties of the polysaccharide and, particularly, of its thickening power. It has been observed that although this enzymatic treatment is particularly efficient when applied to xanthan gum batches of low or mean microgels content, it is nevertheless relatively less efficient when this content is high, particularly when applied to the xanthan gums available in the trade as powders. This limitation of the treatment with a polysaccharase is particularly significant when it is desired to clarify dispersions of powdered xanthan gums in complex waters and particularly in field waters of high salinity and high content of bivalent metal ions.

OBJECTS OF THE INVENTION

A first object of the present invention is to provide an improved method for the clarification of aqueous solutions of xanthan gums, wherein the thickening power of said gums is maintained. Another object of the invention consists in improving the clarification of raw fermentation juices as well as of aqueous dispersions of powdered xanthan gums. Another object of the invention consists in the removal of insoluble cell fragments produced in the fermentation process of these xanthan gums. Another object of the invention consists in improving the injectivity of xanthan gum solutions for use in enhanced oil recovery. Still another object of the invention consists in the removal of microgels and hence in the improvement of the flowing properties of the xanthan gum solutions inside a petroleum formation at a certain distance from the injection well. Finally, another object of the invention consists in the use of solid compositions for improving the limpidity, the injectivity and the flowing of the xanthan gum solutions. Other objects of the invention will be made apparent from the following description.

DESCRIPTION OF THE INVENTION

According to the present invention, it has been found that, by effecting enzymatic treatments of aqueous solutions of xanthan gums, by means of two enzymes having different types of activity, it is possible to substantially increase the filtrability of said solutions as compared to that obtained by a treatment effected separately with one or the other enzyme. The aqueous solutions of xanthan gum, thus made limpid, may be used directly, after dilution at the desired concentration and viscosity, without any further treatment, as flushing fluid for the petroleum formations.

The enzymatic treatment of the present invention may be effected either in the simultaneous presence of an enzyme of the polysaccharase type, also called glucane-hydrolase, and of an enzyme of the protease type at a pH value compatible with a sufficient activity of both enzyme types, or consecutively by means, first, of an enzyme of one of the two above types, at a convenient pH for the selected type, and then by means of an enzyme of the other type, at a convenient pH for this other enzyme type, for example polysaccharase at acid pH, followed with protease at slightly acid, neutral or basic pH, according to the type of protease, or viceversa. The best results are obtained when proceeding in two successive steps, first with the polysaccharase, then with the protease.

The enzymatic treatment of the invention is effected in aqueous medium whose concentration of dissolved salts of alkali and/or alkaline-earth metals is at least $10^{-2}$ equivalent/liter, preferably at least $10^{-1}$ equivalent/liter. However, the higher the salinity of the water used in the treatment, the higher the relative synergic effect obtained. A particular aspect of the present invention consists in the fact that the synergy activity of both enzyme types is also obtained in the presence of bivalent ions, for example $Ca^{++}$ or $Mg^{++}$, and particularly in the field water.

The simultaneous or consecutive enzymatic treatment according to the present invention is preferably effected over a total incubation period of 0.5 to 60 hours and preferably from 4 to 48 hours, at temperatures from room temperature (25° C.) up to about 65° C., preferably from 40° to 60° C. Short treatment times are preferably associated with high temperatures and conversely. When it is chosen to make use of the enzymatic treatment at the highest temperatures, the optimum time is relatively short, for example 16–24 h at 50° C. or 5–10 hours at 60° C. The preferred temperatures range from 40° to 60° C. and preferably will not exceed 65° C., temperature beyond which the enzymes are liable to noticeable deactivation.

A category of enzymes which can be used, according to the present invention, is that of the polysaccharases, i.e. enzymes liable to hydrolyze polysaccharides, as described in the article of M. Rinaudo and M. Milas "Enzymatic hydrolysis of the bacterial polysaccharide xanthan by cellulase" Int. J. Biol. Macromol. 1980 Vol. 2, pages 45 to 48. However, these enzymes, usually sold in the trade under the name of cellulases, are used, in the process conforming to the present invention, under such conditions of pH (3<pH <7), of temperature (25°-65° C.) and of saline concentration (>$10^{-2}$ equivalent/liter) as above indicated, that the characteristics of the xanthan gum by itself are not substantially affected. These conditions have been discussed in the French patent application No. 80/21 395.

The term polysaccharase applies to enzymes having a glucane-hydrolase activity. These enzymes are generally produced by aerobic culture of fungi pertaining to the class of Basidiomycetes or of fungi pertaining to the following species: Aspergillus, Fusarium, Myrothecium, Penicillium, Polyporus, Rhizopus, Sclerotinia, Sporotrichum, Trichoderma, etc. Generally, it is not necessary to purify the enzyme, the raw preparations being perfectly convenient. Examples of industrial preparations are, in particular, and without any limitative character of this listing, the enzymatic extracts called polysaccharases obtained fom Aspergillus or Trichoderma as well as those obtained from Basidiomycetes.

Another category of enzymes which can be used complementarily to the preceding category, consists of the class of bacterial proteases. These proteases are generally produced by micro-organisms of the Bacillus genus such as *B. Subtilis, B. Licheniformis, B. amyloliquifacius* and *B. pumilis* or still of the Streptomyces genus such as *S. fradiae, S. griseus* and *S. rectis.* The enzyme source is however not critical. These proteases have an optimum activity, depending on the case, at slightly acid, neutral or basic pH values, and are then respectively called acid, neutral or alkaline proteases. Of course, in the case of a simultaneous treatment with a polysaccharase and a protease, the enzymatic species will be selected from those having overlapping activity domains, with respect to the pH.

Although the synergic treatment of the present invention is preferably applied to dispersions in salted water of xanthan gums as powder, it is obvious that it can also be applied to fermentation broths, at least to those having a substantial content of microgels. With broths of small microgels content the results are more irregular although this cannot be entirely explained in a satisfactory manner.

The xanthan gums prepared from the so-treated fermentation broths do not require any further enzymatic treatment and the filtrability of their aqueous solutions is considerably improved. The techniques for separating a xanthan gum as powder from a fermentation broth are otherwise well known and consist, for example, in a precipitation with an alcohol miscible with the fermentation juice or still in a drying by lyophilization or solvent evaporation.

The synergy process of the present invention, making use of a simultaneous or consecutive treatment with a polysaccharase and a protease provides first for a degradation of the solid cells and bacteria fragments suspended in the xanthan gum solutions by converting them to hydrosoluble compounds, so as to obtain, finally, a limpid solution. Moreover, and this is more surprising, this synergic treatment makes it possible to remove the translucent microgels, responsible for plugging the petroleum formations at a certain distance from the injection well. During this whole operation of clarification and removal of microgels, the thickening power of the xanthan gum is maintained and the obtained limpid solutions may subsequently, after mere dilution and without further filtration, be injected in the petroleum formations. The injectivity and the flowing properties of said solutions through said formations are clearly improved with respect to the enzyme treatments considered separately as it can be easily proved by the corresponding tests through calibrated filters.

In view of effecting the simultaneous synergic treatment according to the process of the present invention, the following procedure may be applied to starting dispersions in an aqueous phase having the above required salinity, of xanthan gum powders or of dilutions in the same aqueous phase of raw fermentation broths: when necessary, the pH of said solution is adjusted to a value corresponding to the optimum activity of both enzyme types and these two enzymes are added. The temperature is maintained at 25°-65° C. for variable times in order to improve the above described filtrability. When necessary, the pH of the solution is adjusted to the value of the utilization pH and, after dilution to the desired concentration and viscosity, the so-treated solution is ready for use.

When it is desired to effect the enzymatic treatment of the present invention in two steps, the procedure may be as follows: if necessary, the pH of the xanthan gum solution is brought to a value lower than 7 and higher than 3, advantageously from 3 to 6, by means for example of hydrochloric acid, acetic acid or sulfuric acid, then the polysaccharase enzyme is added and the temperature is maintained at 25°-65° C. for the necessary time as above defined and, thereafter, the pH of the solution is brought, by addition for example of sodium hydroxide or potassium hydroxide, to a value higher than 6 and lower than 12, advantageously to a value from 6.5 to 9. After addition of the protease, the temperature is again maintained at 25°-65° C. for the necessary time as above defined. After readjustment of the solution pH to the utilization pH value, and after dilution at the desired concentration and viscosity, the resultant solution is ready for use.

An alternative embodiment of the enzymatic treatment in two steps consists of first adjusting the pH of the solution to a value preferably from 6.5 to 9 and effecting the enzymatic treatment with protease before readjusting the pH to slightly acid values, preferably from 3 to 6, and effecting the enzymatic treatment with polysaccharase.

During the enzymatic treatment of the present invention, the proportion of xanthan gum is, for example, from 0.01 to 4% and, preferably, from 0.04 to 1.5% by weight with respect to water and the proportion of each enzyme is, for example, from 0.001 to 0.5% by weight, preferably from 0.0025 to 0.1% by weight with respect to water, these proportions being not limitative. The minimum enzyme amount to be used is obviously dependent on the amount of active factor in the selected enzymatic preparations.

According to an additional aspect of the present invention, the solid formulations containing xanthan gum and the two enzyme types may be added directly to the field water, thereby avoiding any requirement of separate addition of enzymes to the xanthan gum solution, in view of a simultaneous enzymatic treatment. These solid compositions are of particular interest when the enzymatic clarification must be effected for example in-situ during an enhanced recovery operation. The enzymatic reaction will progress in proportion to the solubilization of the polysaccharide and, with a conveniently selected temperature and pH of the solubilizing water, the enzymatic treatment will not extend the time usually required for the preparattion of the injected xanthan gum solution. It is thus possible to directly obtain a limpid solution having the desired viscosity and which may be directly used without any additional treatment, particularly without any filtration treatment, and which exhibits clearly improved injectivity and filtrability properties in use for enhanced recovery operations.

Such a solid composition may contain, for example, from 1 to 100 and, preferably, from 2 to 30 parts by weight of xanthan gum per part by weight of enzyme mixture.

The following examples illustrate the invention; they must not be considered in any manner as limiting the scope thereof. In these examples, $c_p$ is the polymer concentration, $c_e$ the enzyme concentration and $R_\lambda$ and $R_k$, respectively, the mobility and permeability reductions.

EXAMPLE 1

A solution at 1.6 g/l of polysaccharide powder Rhodopol 23 R (Rhone-Poulenc Industries, France) has been prepared with water containing 20 g/l of NaCl and 0.4 g/l of sodium azide as bacteriostatic agent. After the polymer has been allowed to dissolve for several hours under stirring, the solution is divided into three equal portions:
(a) After having brought the pH of the first portion to 5, 500 mg/l (ppm) of polysaccharase enzyme obtained from Basidiomycete Poria genus, is added. The temperature is brought to 43° C. and, after 3 hours of contact, a portion of the solution is withdrawn for a quick filtrability test. The remaining solution is brought to a pH of 9 and 500 mg/l (ppm) of alkaline protease, obtained from Bacillus Licheniformis, is added and the treatment is continued at 43° C. Samples are taken again after 1 hour and 3.5 hours of this treatment.
(b) The second portion of the polysaccharide solution is also brought to a pH of 5 and, after addition of 500 mg/l (ppm) of polysaccharase, the solution is heated to 43° C. for 16 hours. After withdrawal of a sample and adjustment of the pH to 9,500 mg/l (ppm) of alkaline protease is added and samples are again taken after respectively 4.5 hours and 23 hours of treatment at 43° C.
(c) The third portion of the mother solution is directly brought to a pH of 9 and 500 mg/l (ppm) of alkaline protease are added thereto. Samples are taken respectively after 4 hours and 21 hours of enzymatic treatment at 43° C.

All the samples withdrawn from said various solutions obtained from portions a, b, c are subjected to the quick filtrability test. This test consists of passing the obtained solutions, after dilution to a polymer concentration of 400 ppm with water containing 20 g/l of NaCl, and after adjustment of their pH to 7, through a 0.8 μm Millipore filter ($\phi$=47 mm) under a constant charge of 10 kPa. The results obtained, plotted as curves showing the evolution of the accumulated volumes of filtrate (A) in cm³ versus time (B) in minutes, are reported in FIG. 1. It is observed that:

(1) The enzymatic treatment with only the alkaline protease has but little effect on the filtrability, irrespective of the length of the treatment at pH 9: FIG. 1, curve 0 (4 h at 43° C.) and curve 0' (21 h at 43° C.) substantially identical.
(2) The enzymatic treatment with polysaccharase at pH 5 is already more efficient but the increase of the treatment time at 43° C. only improves to a small extent the filtrability: FIG. 1, curve 1 (3 h at 43° C.) and curve 1' (16 h at 43° C.).
(3) The mixed enzymatic treatment, with polysaccharase at pH 5 followed with protease at pH 9, has a synergic effect on the filtrability. This synergic effect is clearly more important for the solution previously subjected to an extended treatment with polysaccharase: FIG. 1, curve 2' (16 h polysaccharase+4.5 h protease) and curve 2 (3 h polysaccarrase+1 h protease). The increase of the treatment time with protease does not improve except to a small extent the filtrability: FIG. 1, curve 3' (16 h polysaccharase+23 h protease) and curve 3 (3 h polysaccharase+3.5 h protease).

The combined action of polysaccharase+protease accordingly has really a synergic effect on the filtrability. Besides it has been ascertained that, during all these enzymatic treatments, the viscosity of the solutions was substantially unaffected, with a maximum variation of 3% with respect to the untreated solution.

EXAMPLE 2

An enzymatic treatment similar to that of example 1 has been effected on the same polysaccharide powder Rhodopol23R, all other experimental conditions being identical except the salinity of water which has been set at 1 g/l of NaCl.

The results of the filtrability test through 0.8 μm Millipore filters under a constant charge of 10 kPa for the various solutions after enzymatic treatment ($c_p$=400 ppm, pH 7, 1 g/l of NaCl) have been reported in Table I showing the accumulated volumes of filtrates in relation with the filtration time.

The advantages of the synergic treatment according to the invention are consequently also obvious with a lower salinity of the water dissolving the powdered polysaccharide. This results sufficiently from the comparison of lines 3, 5 and 6 as well as of lines 4, 7, 8 of Table 1. At each time the combined treatment is superior to the treatment with the polysaccharase alone and far superior to that effected with the alkaline protease alone.

TABLE 1

| ENZYMATIC TREATMENT | TIME in MINUTES ACCUMULATED VOLUME OF FILTRATE IN cm³ | | | |
|---|---|---|---|---|
| $c_e$ = 500 mg/l | 5 | 10 | 15 | 20 |
| 1 Alkaline protease (4 h at 43° C., pH 9) | 44 | 64 | 76 | 87 |
| 2 Alkaline protease (22 h at 43° C., pH 9) | 46 | 65 | 79 | 91 |
| 3 Polysaccharase (4.5 h at 43° C., pH 5) | 78 | 118 | 150 | 180 |
| 4 Polysaccharase (16 h at 43° C., pH 5) | 136 | 238 | 324 | 394 |
| 5 Polysaccharase (4.5 h at 43° C., pH 5) + Alkaline protease (1.4 h at 43° C., pH 9) | 122 | 206 | 282 | 342 |
| 6 Polysaccharase (4.5 h at 43° C., pH 5) + Alkaline protease | 126 | 222 | 302 | 368 |

TABLE 1-continued

| ENZYMATIC TREATMENT $c_e = 500$ mg/l | TIME in MINUTES ACCUMULATED VOLUME OF FILTRATE IN cm³ | | | |
|---|---|---|---|---|
| | 5 | 10 | 15 | 20 |
| 7 (16.5 h at 43° C., pH 9) Polysaccharase (16 h at 43° C., pH 5) + Alkaline protease (3.5 h at 43° C., pH 9) | 160 | 298 | 428 | 544 |
| 8 Polysaccharase (16 h at 43° C., pH 5) + Alkaline protease (23 h at 43° C., pH 9) | 164 | 314 | 448 | 578 |

EXAMPLE 3

The experimental conditions of example 1 have been reproduced with a polysaccharide powder of food grade Rhodigel 23 (Rhone-Poulenc Industries, France) dissolved in water containing 20 g/l of NaCl at a concentration $c_p = 1,600$ ppm.

The results of quick filtrability tests through 0.8 μm Millipore filters under a constant charge of 10 kPa are summarized in Table 2, expressed as filtrate volumes versus time ($c_p = 400$ ppm, pH 7, 30° C.).

It is observed that a synergic effect on the filtrability is obtained as well when the treatment with basic protease (24 h at 50° C. and at pH 9, line 2) follows the treatment with polysaccharase ($c_e = 500$ ppm, 22 h at 50° C., pH 5), than when the treatment with polysaccharase (24 h at 50° C. and at pH 5, line 4) follows the treatment with basic protease ($c_e = 50$ ppm, 24 h at 50° C., pH 9). The accumulated volumes of filtrate are clearly higher than those obtained for similar treatment times either with polysaccharase or with basic protease (lines 1 and 3 respectively).

TABLE 2

| | ENZYMATIC TREATMENT ($c_e = 500$ mg/l) | TIME IN MINUTES ACCUMULATED VOLUME OF FILTRATE IN cm³ | | | | | | | | |
|---|---|---|---|---|---|---|---|---|---|---|
| | | 5 | 10 | 15 | 20 | 25 | 30 | 35 | 40 | 45 |
| 1 | Polysaccharase (48 h at 50° C., pH 5) | 48 | 72 | 84 | 92 | 98 | 100 | 100 | 100 | 100 |
| 2 | Polysaccharase (22 h at 50° C., pH 5) + Alkaline protease (24 h at 50° C., pH 9) | 136 | 244 | 332 | 402 | 464 | 516 | 566 | 608 | 648 |
| 3 | Alkaline protease (48 h at 50° C., pH 9) | 8 | 8 | 10 | 10 | 10 | 10 | 10 | 10 | 10 |
| 4 | Alkaline protease (24 h at 50° C., pH 9) + Polysaccharase (24 h at 50° C., pH 5) | 120 | 210 | 286 | 350 | 404 | 452 | 516 | 538 | 576 |

TABLE 3

| ENZYMATIC TREATMENT ($c_e = 500$ mg/l) | TIME IN MINUTES ACCUMULATED VOLUME OF FILTRATE IN cm³ | | | | | |
|---|---|---|---|---|---|---|
| | 5 | 10 | 15 | 20 | 25 | 30 |
| 1 Polysaccharase (48 h at 50° C., pH 5) | 60 | 96 | 126 | 152 | 174 | 192 |
| 2 Polysaccharase (20 h at 50° C., pH 5) + Alkaline protease (23 h at 50° C., pH 9) | 148 | 290 | 412 | 526 | 632 | 726 |

A xanthan gum powder has been separated from said broth treated with enzymes, by precipitation with isopropyl alcohol, redissolution in water and drying by lyophilisation. The powder then solubilized at a concentration $c_p 32$ 400 ppm in water containing 20 g/l of NaCl and subjected to the same filtration test through a 0.8 μm Millipore filter under 10 kPa no longer suffers from any propensity to plugging. This proves that the synergic enzymatic treatment of the present invention, not only provides for a substantial improvement of the filtrability of the fermentation broths, but also makes it possible to avoid the tendency to microgels formation during the separation step as powder from the broth when this treatment has been effected previously on said fermentation broth.

EXAMPLE 5

This example has the purpose, on the one hand, to show the synergic activity of other enzymes and particularly of a neutrase (neutral protease) and, on the other hand, to ascertain that the synergic enzymatic treatment may be effected in a single step at a pH value close to the neutrality (pH 6.0).

There are prepared two solutions at 1,600 ppm of

EXAMPLE 4

The experimental conditions of example 1 have been reproduced with an industrial fermentation broth Flocon 1035 (Pfizer Corporation, USA) diluted at $c_p = 1,600$ ppm by means of water containing 20 g/l of NaCl.

The results of the filtrability tests through 0.8 μm Millipore filters under a constant charge of 10 kPa are reported in Table 3. It can be seen that with a broth of xanthan gum, having a very bad filtrability, the synergic treatment polysaccharase-alkaline protease (line 2) is more efficient than the only treatment with polysaccharase (line 1).

KELZAN MF (polysaccharide powder of Kelco Company, USA) in waters having respectively salinities of 1 g/l and 20 g/l of NaCl. Each of these mother solutions is then again divided into three substantially equal portions and the following successive operations are effected for each salinity:

(a) the first portion of each mother solution is adjusted to a pH of 7, then 500 mg/l of neutral protease obtained from Bacillus subtilis is added thereto and the solution is subjected to a thermal treatment at 50° C. for 22 hours. At the end of this time, a sample of the solution is taken, its pH is adjusted to 5 by means of hydrochloric acid and 500 mg/l of polysaccharase obtained from Aspergillus niger is added thereto. The so obtained two solutions are then heated for 22 hours at 43° C. and, after that, diluted with water of NaCl content corresponding to the polymer concentration of 400 ppm, their pH being adjusted to 7. These solutions are then tested in the usual manner through a 0.8 μm Millipore filter under 10 kPa (lines 1 and 2 of Tables 4 and 5), (b) the pH of another portion of each mother solution is brought to 5 before adding 500 mg/l of the same polysaccharase as above and subjecting it to a thermal treatment for 22 hours at 50° C. After this time, the pH of the solution is adjusted to 7, 500 mg/l of the above mentioned neutral protease is added and the thermal treatment is continued again for 22 hours. After dilution at $c_p=400$ ppm, the filtrability of the solution is tested (lines 3 of Tables 4 and 5), (c) 500 mg/l of polysaccharase of *Aspergillus niger* and 500 mg/l of neutral protease of *Bacillus subtilis* are added to each mother solution, brought to a pH of 6. After a thermal treatment for 66 hours at 50° C., the solution is brought to the desired concentration $c_p=400$ ppm and pH 7 before being subjected to the filtration test (lines 4 of Tables 4 and 5).

(3) The simultaneous treatment with the two types of enzymes is more efficient than the action of a single of these two enzyme types, but the improvement obtained is generally smaller than with the successive treatment. This latter observation is probably related to the fact that the treatment is not effected at the optimum pH for each enzyme.

EXAMPLE 6

This example has for object to prove the synergic activity which may be obtained when starting with a polysaccharase and an acid protease. A solution at 1,600 ppm of polysaccharide powder of food grade Rhodigel 23 has first been prepared in water containing 20 g/l of NaCl. The pH of the solution has then been adjusted to 5 and 500 mg/l of the polysaccharase obtained from *Trichoderma viride* have been added. After 16 hours of thermal treatment at 43° C., the obtained limpid solution has been divided into two substantially equal portions:

(a) the first solution has been adjusted to a pH of 9 and 500 mg/l of alkaline protease, obtained from *Bacillus*

TABLE 4

Enzymatic treatments in water containing 1 g/l of NaCl

| | ENZYMATIC TREATMENT ($c_e$ = 500 ppm) | TIME IN MINUTES — ACCUMULATED VOLUME OF FILTRATE IN cm³ | | | | | | | |
|---|---|---|---|---|---|---|---|---|---|
| | | 5 | 10 | 15 | 20 | 25 | 30 | 35 | 40 |
| 1 | Neutral protease (44 h at 50° C., pH 7) | 72 | 120 | 140 | 162 | 182 | 200 | 216 | 230 |
| 2 | Neutral protease (22 h at 50° C., pH 7) + Polysaccharase (22 h at 50° C., pH 5) | 134 | 234 | 322 | 400 | 470 | 534 | 588 | 646 |
| 3 | Polysaccharase (22 h at 50° C., pH 5) + Neutral protease (22 h at 50° C., pH 7) | 156 | 274 | 376 | 466 | 548 | 616 | 684 | 744 |
| 4 | Simultaneous treatment (66 h at 50° C., pH 6) | 96 | 158 | 204 | 244 | 274 | 302 | 324 | 348 |

TABLE 5

Enzymatic treatments in water containing 20 g/l of NaCl

| | ENZYMATIC TREATMENT ($c_e$ = 500 ppm) | TIME IN MINUTES — ACCUMULATED VOLUME OF FILTRATE IN cm³ | | | | | | | |
|---|---|---|---|---|---|---|---|---|---|
| | | 5 | 10 | 15 | 20 | 25 | 30 | 35 | 40 |
| 1 | Neutral protease (44 h at 50° C., pH 7) | 3 | 5 | 6 | 8 | 9 | 10 | 11 | 12 |
| 2 | Neutral protease (22 h at 50° C., pH 7) + Polysaccharase (22 h at 50° C., pH 5) | 68 | 104 | 130 | 148 | 164 | 178 | 188 | 196 |
| 3 | Polysaccharase (22 h at 50° C., pH 5) + Neutral protease (22 h at 50° C., pH 7) | 96 | 154 | 200 | 238 | 270 | 298 | 324 | 344 |
| 4 | Simultaneous treatment (66 h at 50° C., pH 6) | 68 | 104 | 130 | 152 | 170 | 186 | 202 | 214 | the results of the filtrability tests show that:

(1) The action of the neutral protease on the filtrability is negligible in water containing 20 g/l of NaCl but appears to be better in the case of a lower salinity.

(2) The synergic action of polysaccharase-neutral protease is beneficial to the filtrability of xanthan gum solutions in both types of water, with nevertheless a better filtrability in the polysaccharase-neutral protease order as compared with the neutral protease-polysaccharase order. This synergic activity is greater for water of lower salinity.

*licheniformis,* have been added thereto. After 6 hours of treatment at 43° C., the pH of the obtained solution is adjusted to 7 and the solution, diluted with water at 20 g/l of NaCl at the concentration $c_p=400$ ppm, is subjected to the usual filtration test (line 2 of Table 6).

(b) the second solution has been adjusted to a pH of 6.5 and 500 mg/l of acid protease, obtained from *Bacilus subtilis,* have been added thereto. Samples are taken respectively after 6 h, 23 h and 33 h of treatment at 43° C., diluted at the concentration of 400 ppm of polymer, adjusted to pH 7 and then tested (lines 3, 4 and 5 of Table 6).

The results of the filtrability tests through a 0.8 μm Millipore filter under 10 kPa have been compared in Table 6 to the result obtained with a solution subjected to a treatment with polysaccharase for 30 hours at 43° C. and at pH 5 (line 1).

to those of part (a) above. The dilution to $c_p = 400$ ppm of xanthan gum for the filtrability test is also made with the field water and after readjustment of the pH to 7, the solutions which have been subjected to the action of alkaline protease, respectively for 22 and 40 h at 43° C., in addition to the treatment with polysaccharase, are tested (lines 2 and 3 of Table 8).

TABLE 6

| | ENZYMATIC TREATMENT ($C_e$ = 500 ppm) | TIME IN MINUTES ACCUMULATED VOLUME OF FILTRATE IN cm³ | | | | | | |
|---|---|---|---|---|---|---|---|---|
| | | 5 | 10 | 15 | 20 | 25 | 30 | 35 |
| 1 | Polysaccharase (30 h at 43° C., pH 5) | 50 | 76 | 193 | 107 | 117 | 125 | 131 |
| 2 | Polysaccharase (16 h at 43° C., pH 5) + Alkaline protease (6 h at 43° C., pH 9) | 142 | 253 | 345 | 420 | — | — | — |
| 3 | Polysaccharase (16 h at 43° C., pH 5) + Acid protease (6 h at 43° C., pH 6.5) | 74 | 114 | 144 | 168 | 190 | 206 | 217 |
| 4 | Polysaccharase (16 h at 43° C., pH 5) + Acid protease (23 h at 43° C., pH 6.5) | 82 | 128 | 162 | 189 | 214 | 234 | 250 |
| 5 | Polysaccharase (16 h at 43° C., pH 5) + Acid protease (33 h at 43° C., pH 6.5) | 102 | 164 | 210 | 248 | 281 | 311 | 338 |

It is observed that the treatment with acid protease consecutively to a treatment with polysaccharase is less efficient than the corresponding treatment with basic protease. Nevertheless, the synergic effect becomes substantial when increasing the enzymatic treatment time.

EXAMPLE 7

This example has for object to ascertain that the synergic enzymatic treatment of the present invention may also be conducted in the presence of water of the field. Two cases have been considered:

(a) Direct dispersion of the xanthan gum powder Rhodopol 23R ($c_p = 1,600$ ppm) in the water of the field whose total salinity is about 30 g/l comprising 8.6 g/l of sodium ions, 1.3 g/l of calcium ions and 0.29 g/l of magnesium ions. Adjustment of the pH to 5 and treatment with 500 mg/l of polysaccharase obtained from Basidiomycete Poria genus at 43° C. for 22 hours, readjustment to pH 9 and treatment by means of 500 mg/l of alkaline protease obtained from *Bacillus licheniformis* for variable times, respectively 22 and 80 hours. The obtained solutions are diluted at $c_p = 400$ ppm with water from the field, adjusted to pH 7 and tested in the usual manner (lines 2 and 3 of Table 7). The results are compared to that resulting from the action of polysaccharase alone (48 h at 43° C., pH 5) (line 1, Table 7).

(b) Predispersion of the same powder at the concentration $c_p = 4,000$ ppm in water containing 1 g/l of NaCl, followed with successive enzymatic treatments with polysaccharase at pH 5 and with protease at pH 9, the enzyme types and their concentrations being identical to those of part (a) above. The dilution to $c_p = 400$ ppm of xanthan gum for the filtrability test is also made with the field water and after readjustment of the pH to 7, the solutions which have been subjected to the action of alkaline protease, respectively for 22 and 40 h at 43° C., in addition to the treatment with polysaccharase, are tested (lines 2 and 3 of Table 8).

The results are compared with those of the same initial solution ($c_p = 4,000$ ppm, 1 g/l of NaCl) exclusively subjected to the treatment with polysaccharase (48 hours at 43° C., pH 5) (line 1, Table 8).

It is observed that, although the predispersion and the synergic enzymatic treatment in water of low salinity generally gives the best results in the filtrability test effected on the final solution, the synergic effect is also obtained with very good results of the filtrability test by the direct action on the solution of polysaccharide in the field water.

In order to ascertain the improvement obtained by means of the synergic treatment polysaccharase-protease, a comparative flowing test at low but constant flow rate (q = 3 cc/h) has been effected through 8 μm Millipore filters with solutions previously subjected to the treatment by polysaccharase (48 h at 43° C.), and with those subjected to the synergic action of polysaccharase (22 h at 43° C.) and alkaline protease (40 h at 43° C.). The results of the flowing test at 43° C., in the presence of field water, show the continuence of a substantial plugging of the two series of successive filters when applying the treatment with polysaccharase alone ($R_\lambda > 100$) which is however less important than that produced by a solution not treated with enzymes ($R_\lambda > 800$); no plugging was detected and, on the contrary, a stabilization of the mobility reduction values ($R_\lambda = 20$) was obtained on the two series of filters with the solution subjected to the synergic treatment. This shows the substantially complete removal of the microgels during the combined treatment polysaccharase-protease in the presence of the field water.

TABLE 7

DIRECT SOLUBILIZATION IN WATER OF THE FIELD
($c_p$ = 1 600 ppm)

| ENZYMATIC TREATMENT ($c_e$ = 500 ppm) | TIME IN MINUTES ACCUMULATED VOLUME OF FILTRATE IN cm³ | | | | | | | |
|---|---|---|---|---|---|---|---|---|
| | 5 | 10 | 15 | 20 | 25 | 30 | 35 | 40 |
| 1 Polysaccharase (48 h at 43° C., pH 5) | 38 | 58 | 72 | 80 | 86 | 90 | 90 | 90 |
| 2 Polysaccharase (22 h at 43° C., pH 5) + Alkaline protease (22 h at 43° C., pH 9) | 50 | 82 | 106 | 126 | 144 | 160 | 174 | 188 |
| 3 Polysaccharase (22 h at 43° C., pH 5) + Alkaline protease (22 h at 43° C., pH 9) | 128 | 220 | 292 | 352 | 400 | 440 | 478 | 514 |

TABLE 8

PREDISPERSION IN WATER AT 1 g/l of NaCl
($c_p$ = 4 000 ppm)

| ENZYMATIC TREATMENT ($c_e$ = 500 ppm) | TIME IN MINUTES ACCUMULATED VOLUME OF FILTRATE IN cm³ | | | | | |
|---|---|---|---|---|---|---|
| | 5 | 10 | 15 | 20 | 25 | 30 |
| 1 Polysaccharase (48 h at 43° C., pH 5) | 60 | 106 | 148 | 182 | 214 | 246 |
| 2 Polysaccharase (22 h at 43° C., pH 5) + Alkaline protease (22 h at 43° C., pH 9) | 140 | 264 | 376 | 480 | 576 | 664 |
| 3 Polysaccharase (22 h at 43° C., pH 5) + Alkaline protease (40 h at 43° C., pH 9) | 144 | 276 | 394 | 496 | 590 | 682 |

EXAMPLE 8

This example has for object to explain the filtrability improvement obtained by the synergic treatment of the present invention and, in particular to differentiate the specific action of the two enzyme types on the two main factors responsible of the plugging of petroleum formations by aqueous solutions of xanthan gums, i.e. the insoluble cell fragments, on the one hand, and the translucent microgels, on the other hand.

A solution at 400 ppm by weight of polysaccharide powder Rhodopol 23R in water at 20 g/l of NaCl is first clarified by filtration under standard conditions through successive Millipore filters of 3 µm and 0.8 µm under a charge of 100 kPa. A part of the obtained slightly opalescent solution is subjected to the usual filtration test (line 1 of Table 9), the remaining solution being divided into three substantially equal parts. The following enzymatic treatments are then applied and the obtained solutions are then also tested:

(a) treatment by means of 500 mg/l of alkaline protease obtained from *Bacillus licheniformis* for 48 h at 43° C. and at pH 9, then test at pH 7 (line 2 of Table 9), (b) treatment by means of 500 mg/l of polysaccharase for 48 h at 43° C. and at pH 5, then test at pH 7 (line 3 of Table 9), (c) successive treatment with polysaccharase (23 h at 43° C., pH 5) and alkaline protease (23 h at 43° C., pH 9), then test at pH 7 (line 4 of Table 9).

The action of the alkaline protease slightly improves filtrability as compared with the solution merely clarified by filtration. This action is to be attributed to the digestion of insoluble particles of protein origin which have not been completely removed by the filtration.

The action of the polysaccharase seems particularly beneficial for the removal of microgels which, in view of their deformability, are the determining factor of filter plugging when the pressure decreases.

The synergic treatment with polysaccharase-protease produces a solution of almost perfect filtrability. The substantially complete removal of the microgels has been ascertained during flowing tests at constant flow rate effected through various calibrated filters of 3 µm (Millipore filters and Nuclepore membranes), the permeability reduction values ($R_k$) being close to unity, as well as during the flow through a porous not consolidated carborundum medium, having the following characteristics:

Length 3.6 cm, diameter 1.3 cm, permeability 97 mD, porosity 51.7%. The values of $R_{80}$ = 5.2 and $R_k$ = 1.25 in the newtonian zone obtained in the latter flow experiment are characteristic of a very substantial reduction of the microgels content, and the flow through a porous medium of low permeability takes place without any plugging.

TABLE 9

| ENZYMATIC TREATMENT ($c_e$ = 500 ppm) | TIME IN MINUTES ACCUMULATED VOLUME OF FILTRATE IN cm³ | | | | | |
|---|---|---|---|---|---|---|
| | 5 | 10 | 15 | 20 | 25 | 30 |
| 1 Without treatment | 18 | 28 | 33 | 38 | 40 | 41 |
| 2 Alkaline protease (48 h at 43° C., pH 9) | 82 | 110 | 124 | 132 | 136 | 140 |
| 3 Polysaccharase (48 h at 43° C., pH 5) | 132 | 230 | 316 | 394 | 468 | 534 |
| 4 Polysaccharase (23 h at 43° C., pH 5) + Alkaline protease (23 h at 43° C., pH 9) | 162 | 298 | 418 | 526 | 620 | 698 |

What is claimed is:

1. A process for the treatment of a xanthan gum in order to improve the filtrability of its aqueous solutions, comprising enzymatically treating an aqueous solution of a xanthan gum having a total concentration of dissolved alkali and alkaline-earth metal salts of at least $10^{-2}$ equivalents/liter with at least two enzymes of different types, one being a polysaccharase and another being a protease, under conditions compatible with the activity of said enzymes.

2. A process according to claim 1, wherein two types of enzymes are used simultaneously under such conditions that both types are simultaneously active.

3. A process according to claim 1, wherein the enzymatic treatment is effected in two successive steps, first with an enzyme of a first type and then with an enzyme of the other type, the conditions being so selected in each step that the selected enzyme type is active in said step.

4. A process according to claim 3, wherein the first step comprises a treatment with a polysaccharase and the second step a treatment with a protease.

5. A process according to claim 4, wherein the first step is effected with a polysaccharase at a pH from 3 to 7 and the second step with an alkaline protease at a pH from 7 to 12.

6. A process according to claim 3, wherein the polysaccharase is an enzyme obtained by culture of a fungus belonging to the Basidiomycetes class or to the Aspergillus or *Trichoderma genera*.

7. A process according to claim 3, wherein the protease is an enzyme obtained by culture of a microorganism of the Bacillus type.

8. A process according to claim 1, wherein the enzymatic treatment is effected in 0.5 to 60 hours at a temperature from 25° to 65° C.

9. A process according to claim 1, which further comprises separating and recovering the xanthan gum in the solid state from the resultant treated solution.

10. A process according to claim 1, wherein the proportion of enzyme of each type is from 0.001 to 0.5% of the water weight of the aqueous solution of xanthan gum.

11. A process according to claim 1, wherein the aqueous solution of xanthan gum subjected to the treatment is a solution obtained by dissolving xanthan powder in water.

12. A process according to claim 1, wherein the aqueous solution of xanthan gum subjected to the treatment is a fermentation broth.

13. A process according to claim 1, wherein the treatment is effected with an aqueous solution of xanthan gum prepared by dissolving in water a solid composition containing, in admixture, the xanthan gum powder to be treated and the enzymes of both types.

14. A process according to claim 1, wherein said total concentration of dissolved salts is at least $10^{-1}$ equivalents/liter.

15. A process according to claim 6, wherein the protease is an enzyme obtained by culture of a microorganism of the Bacillus type.

16. A process according to claim 5, wherein the polysaccharase is an enzyme obtained by culture of a fungus belonging to the Basidiomycetes class or to the Aspergillus or *Trichoderma genera;* and the protease is an enzyme obtained by culture of a microorganism of the Bacillus type.

17. A process according to claim 16, wherein the polysaccharase is obtained from *Basidiomycetes poria* and the protease is obtained from *Bacillus licheniformis.*

18. A process according to claim 1, wherein said enzymatic treatment is effected with a solution of said xanthan gum in field water.

19. A process according to claim 1, wherein the resultant treated solution has a viscosity differing by at most 3% from its viscosity prior to enzymatic treatment.

* * * * *